US00PP35053P2

(12) United States Plant Patent
van den Hoogen

(10) Patent No.: US PP35,053 P2
(45) Date of Patent: Mar. 21, 2023

(54) ***VERONICA* PLANT NAMED 'ALLVSPLA'**

(50) Latin Name: ***Veronica longifolia* X *Veronica spicata***

Varietal Denomination: 'Allvspla'

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 17/899,480

(22) Filed: Aug. 30, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Veronica* plant named 'Allvspla', characterized by its upright plant habit; moderately vigorous to vigorous growth habit and moderate growth rate; freely basal branching habit; dark green-colored leaves; freely flowering habit; hemispherical compound inflorescences with numerous light purple-colored flowers; and good performance as a garden plant and cut flower.

2 Drawing Sheets

Figure 1:
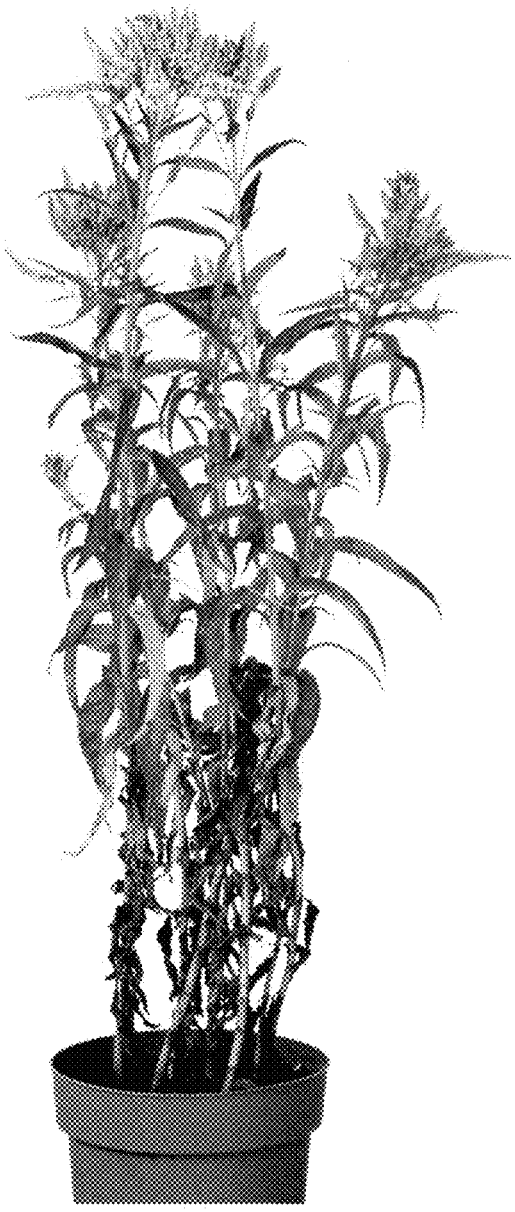

Botanical designation: *Veronica longifolia* X *Veronica spicata.*
Cultivar denomination: 'ALLVSPLA'.

PRIOR DISCLOSURES BY INVENTOR/APPLICANT & ASSIGNEE

An European Community Plant Breeder's Rights application for the instant plant was filed by the Assignee, Allplants Holding B.V. of Cuijk, The Netherlands on Sep. 15, 2021, application number 2021/2285. Foreign priority is not claimed to this application.

BACKGROUND OF THE INVENTION

The present invention relates to a new and distinct cultivar of *Veronica* plant, botanically known as *Veronica longifolia* X *Veronica spicata*, typically grown as a garden plant or cut flower and hereinafter referred to by the name 'Allvspla'.

The new *Veronica* plant is a product of a planned breeding program conducted by the Inventor in Naivasha, Kenya. The objective of the breeding program is to create new attractive *Veronica* plants with attractive flowers, good garden performance and cut flower potential.

The new *Veronica* plant was discovered and selected by the Inventor as naturally-occurring whole plant mutation of *Veronica longifolia* X *Veronica spicata* 'Allfount', disclosed in U.S. Plant Pat. No. 31,554, in a controlled nursery environment in Naivasha, Kenya in June, 2018.

Asexual reproduction of the new *Veronica* plant by terminal stem cuttings in a controlled environment in Naivasha, Kenya, since June, 2018 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvspla'. These characteristics in combination distinguish 'Allvspla' as a new and distinct *Veronica* plant:

1. Upright plant habit.
2. Moderately vigorous to vigorous growth habit and moderate growth rate.
3. Freely basal branching habit.
4. Dark green-colored leaves.
5. Freely flowering habit.
6. Hemispherical compound inflorescences with numerous light purple-colored flowers.
7. Good performance as a garden plant and cut flower.

Plants of the new *Veronica* differ primarily from plants of the female parent, 'Allfount', primarily in flower color as plants of the new *Veronica* have light purple-colored flowers whereas plants of 'Allfount' have violet-colored flowers.

Plants of the new *Veronica* can be compared to plants of *Veronica longifolia* X *Veronica spicata* 'Allvwav', disclosed in a U.S. Plant Patent application filed concurrently. In side-by-side comparisons, plants of the new *Veronica* differ primarily from plants of 'Allvwav' in flower color as plants of the new *Veronica* have light purple-colored flowers whereas plants of 'Allvwav' have white-colored flowers. In addition, plants of the new *Veronica* are taller than plants of 'Allvwav'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'Allvspla' grown in a container.

Figure 3:
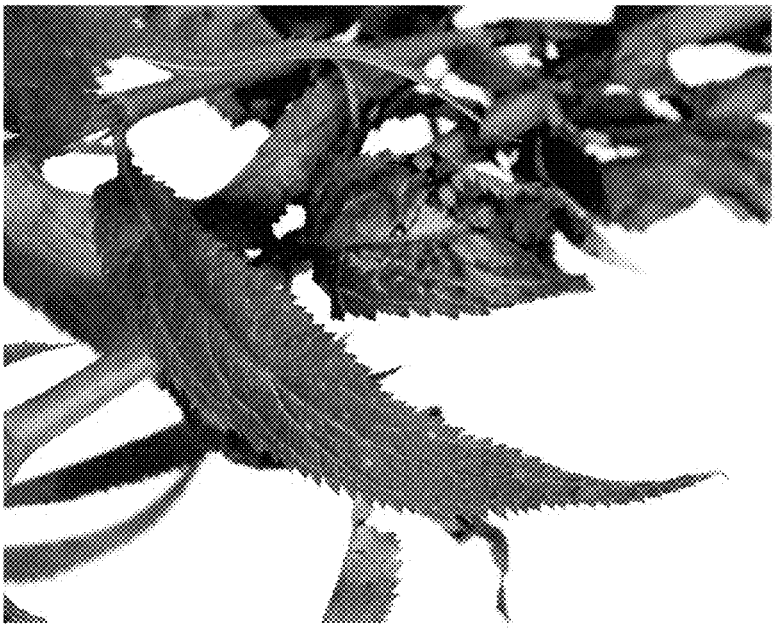
Figure 2:
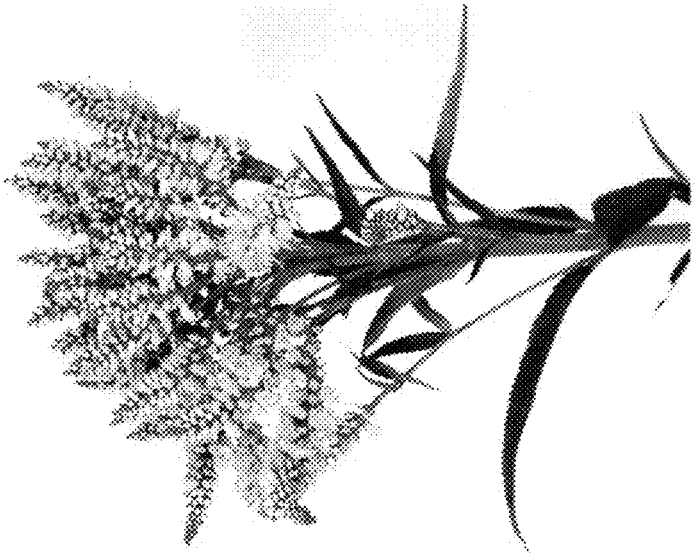

The photographs on the second sheet are close-up views of typical inflorescences (FIG. 2) and typical leaves (FIG. 3) of 'Allvspla'.

DETAILED BOTANICAL DESCRIPTION

Plants used for the aforementioned photographs and following description were grown in ground beds and 19-cm containers during the summer in a outdoor nursery in Cuijk, The Netherlands and under cultural practices typical of commercial *Veronica* production. During the production of the plants, day temperatures ranged from 0° C. to 25° C. and night temperatures ranged from −5° C. to 15° C. Plants were 18 months old when the photographs and the description were taken. In the following description, color references are made to The Royal Horticultural Society Colour Chart, 2015 Edition, except where general terms of ordinary dictionary significance are used.

Botanical classification: *Veronica longifolia* X *Veronica spicata* 'Allvspla'.

Parentage: Naturally-occurring whole plant mutation of *Veronica longifolia* X *Veronica spicata* 'Allfount', disclosed in U.S. Plant Pat. No. 31,554.

Propagation:

*Type cutting*.—Terminal stem cuttings.

*Time to initiate roots, summer*.—About two weeks at temperatures ranging from 10° C. to 25° C.

*Time to produce a rooted young plant, summer*.—About 28 to 34 days at temperatures ranging from 10° C. to 25° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Upright plant habit with compound hemispherical inflorescences; overall plant shape, narrowly oblong to narrowly inverted triangular; moderately vigorous to vigorous growth habit and moderate growth rate.

*Plant height, soil level to top of foliar plane*.—About 76 cm.

*Plant height, soil level to top of floral plane*.—About 83 cm.

*Plant width*.—About 56.3 cm.

*Lateral branch description*.—Branching habit: Freely basal branching habit with about eight basal stems per plant; pinching will enhance lateral branching. Length (excluding inflorescence): About 67.4 cm. Diameter: About 4.5 mm. Internode length: About 6.1 cm. Strength: Strong. Aspect: Erect to about 10° from vertical. Texture and luster: Densely pubescent; slightly glossy. Color, developing: Close to 145A. Color, developed: Close to 146D.

Leaf description:

*Arrangement*.—Opposite or in whorls of three, simple.

*Length*.—About 12.5 cm.

*Width*.—About 3 cm.

*Shape*.—Lanceolate; moderately to strongly carinate.

*Apex*.—Narrowly acute.

*Base*.—Truncate.

*Margin*.—Serrate; not lobed.

*Texture and luster, upper surface*.—Sparsely to moderately pubescent; not rugose; slightly glossy.

*Texture and luster, lower surface*.—Densely pubescent; not rugose; matte.

*Venation pattern*.—Pinnate.

*Color*.—Developing leaves, upper surface: Close to 143A to slightly darker than 143A. Developing leaves, lower surface: Close to 144A. Fully expanded leaves, upper surface: Close to NN137B; venation, close to 146B. Fully expanded leaves, lower surface: Close to 147B; venation, close to 145A.

*Petioles*.—Length: About 9 mm. Diameter: About 2 mm by 3.5 mm. Strength: Strong. Texture and luster, upper and lower surfaces: Moderately pubescent; slightly glossy. Color, upper surface: Close to 152B; margins, close to 144B. Color, lower surface: Close to 145A; margins, close to 143C.

Flower description:

*Flower arrangement and shape*.—Single campanulate flowers arranged on hemispherical compound terminal racemes; flowers face mostly outwardly.

*Flowering habit*.—Freely flowering habit with about 1,500 flowers developing per inflorescence and about 12,000 flowers developing per plant during the flowering season.

*Fragrance*.—None detected.

*Natural flowering season*.—Long flowering period; plants flower continuously from the summer until the autumn in The Netherlands; plants begin flowering about 13 weeks after planting.

*Flower longevity*.—Individual flowers last about seven days and inflorescences last about three weeks on the plant and about two weeks as a cut flower; flowers not persistent.

*Flower buds*.—Length: About 4 mm. Diameter: About 2 mm. Shape: Elliptical. Texture and luster: Smooth, glabrous; matte. Color: Close to N82D and proximally, close to 85D; developing calyx, close to N138C.

*Inflorescence height* (*length*).—About 12.4 cm.

*Inflorescence diameter*.—About 11.9 cm.

*Flower diameter*.—About 5 mm by 5 mm.

*Flower length*.—About 8 mm.

*Throat diameter*.—About 2 mm.

*Tube length*.—About 2 mm.

*Tube diameter*.—About 2 mm.

*Petals*.—Quantity and arrangement: Four in a single whorl; upper and lateral petals larger than the lower petal; petals fused about 40% of the petal length from the base. Length, upper petals: About 5 mm. Length, lower petals: About 4.5 mm. Width, upper petals: About 3 mm. Width, lower petals: About 2 mm. Shape, all petals: Obovate; moderately concave. Apex, all petals: Obtuse. Margin, all petals: Entire; not undulate. Texture and luster, all petals, upper and lower surfaces: Smooth, glabrous; not rugose; matte. Texture and luster, throat: Smooth, glabrous; matte.

Texture and luster, tube: Densely pubescent; matte. Color, all petals: When opening and fully opened, upper surface: Close to 85A to 85B; venation, close to 85A to 85B; color does not change with subsequent development. When opening and fully opened, lower surface: Close to 85B; venation, close to 85B; color does not change with subsequent development. Throat: Close to 85C to 85D; venation, close to 85C to 85D. Tube: Close to 85D; venation, close to 85D.

*Sepals*.—Quantity and arrangement: Four arranged in a single whorl and fused at the base. Length: About 2 mm to 2.5 mm. Width: About 1 mm. Shape: Narrowly ovate. Apex: Acute. Base: Broadly cuneate, fused. Margin: Entire. Texture and luster, upper and lower surfaces: Smooth, glabrous; matte. Color: When opening, upper surface: Close to 143A. When opening, lower surface: Close to N138C. Fully opened, upper surface: Close to 143A. Fully opened, lower surface: Close to N138B.

*Peduncles*.—Length: About 10.7 cm. Diameter: About 3 mm. Aspect: Upright; secondary peduncles, about 25° from main peduncle axis. Strength: Strong. Texture and luster: Densely pubescent; slightly glossy. Color: Close to 144A.

*Pedicels*.—Length: About 1.5 mm. Diameter: About 0.5 mm. Aspect: About 60° from peduncle axis. Strength: Moderately strong. Texture and luster: Densely pubescent; slightly glossy. Color: Close to 144B.

*Flower bracts*.—None observed.

*Reproductive organs*.—Stamens: Quantity per flower: Typically two. Filament length: About 5 mm. Filament color: Close to a blend of 85C and 85D. Anther size: About 2 mm by 1 mm. Anther shape: Broadly sagittate; dorsifixed. Anther color: Close to 4C. Pollen amount: Scarce. Pollen color: Close to 2D. Pistils: Quantity per flower: One. Pistil length: About 7 mm. Stigma diameter: About 2 mm. Stigma shape: Club-shaped. Stigma color: Close to N155A. Style length: About 6.5 mm. Style color: Close to N155A. Ovary color: Close to 144C.

*Seeds and fruits*.—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'Allvspla' as illustrated and described.

* * * * *